United States Patent
Kurokawa et al.

(10) Patent No.: US 10,280,126 B2
(45) Date of Patent: May 7, 2019

(54) METHOD FOR PRODUCING CONJUGATED DIENE

(71) Applicants: JXTG NIPPON OIL & ENERGY CORPORATION, Tokyo (JP); NATIONAL UNIVERSITY CORPORATION SAITAMA UNIVERSITY, Saitama (JP)

(72) Inventors: Hideki Kurokawa, Saitama (JP); Tatsuya Ichijo, Tokyo (JP); Nobuhiro Kimura, Tokyo (JP)

(73) Assignees: JXTG NIPPON OIL & ENERGY CORPORATION, Tokyo (JP); NATIONAL UNIVERSITY CORPORATION SAITAMA UNIVERSITY, Saitama (JP)

( * ) Notice: Subject to any disclaimer, the term of this patent is extended or adjusted under 35 U.S.C. 154(b) by 0 days.

(21) Appl. No.: 15/559,625

(22) PCT Filed: Mar. 18, 2016

(86) PCT No.: PCT/JP2016/058773
§ 371 (c)(1),
(2) Date: Sep. 19, 2017

(87) PCT Pub. No.: WO2016/152796
PCT Pub. Date: Sep. 29, 2016

(65) Prior Publication Data
US 2018/0065901 A1    Mar. 8, 2018

(30) Foreign Application Priority Data
Mar. 26, 2015   (JP) ................................ 2015-064163

(51) Int. Cl.
*C07C 5/333*     (2006.01)
*B01J 23/62*     (2006.01)
*C07C 11/167*    (2006.01)
*B01J 21/02*     (2006.01)

(52) U.S. Cl.
CPC ............. *C07C 5/3337* (2013.01); *B01J 21/02* (2013.01); *B01J 23/62* (2013.01); *C07C 11/167* (2013.01); *C07C 2523/62* (2013.01)

(58) Field of Classification Search
CPC ...... C07C 5/3337; C07C 11/167; B01J 23/62; B01J 21/02
See application file for complete search history.

(56) References Cited

U.S. PATENT DOCUMENTS

2014/0309470 A1* 10/2014 Park ...................... B01J 23/626
585/660

FOREIGN PATENT DOCUMENTS

| JP | S57140730 A | 8/1982 |
|----|-------------|--------|
| JP | S59161324 A | 9/1984 |
| JP | S60001139 A | 1/1985 |
| JP | S60019722 A | 1/1985 |
| JP | 2003220335 A | 8/2003 |
| JP | 2012111699 A | 6/2012 |
| JP | 2014205135 A | 10/2014 |

OTHER PUBLICATIONS

Machine translation of Kikuchi et al. "Effect of Sn Addition on n-Butane Dehydrogenation over Aluina-supported Pt Catalysts Prepared by Co-impregnation and Sol-gel Methods" Journal of the Japan Petroleum Institute, 2012, vol. 55, No. 3 p. 206-213 (Year: 2012).*
Iori Kikuchi et al., "Effect of Sn Addition on n-Butane Dehydrogenation over Alumina-supported Pt Catalysts Prepared by Co-impregnation and Sol-gel Methods", Journal of the Japan Petroleum Institute, 2012, vol. 55, No. 3, p. 206-p. 213.
International Search Report from Patent Application No. PCT/JP2016/058773 dated Jun. 14, 2016.
International Preliminary Report on Patentability from Patent Application No. PCT/JP2016/058773 dated Sep. 26, 2017.
Written Opinion of the International Searching Authority from Patent Application No. PCT/JP2016/058773 dated Jun. 14, 2016.

* cited by examiner

*Primary Examiner* — Brian A McCaig
*Assistant Examiner* — Jason Y Chong
(74) *Attorney, Agent, or Firm* — Greenblum & Bernstein, P.L.C.

(57) ABSTRACT

A method for producing a conjugated diene according to one aspect of the present invention comprises a step of contacting a raw material gas containing an olefin with a dehydrogenation catalyst to obtain a product gas containing a conjugated diene. In the production method, the dehydrogenation catalyst contains Al, a group 14 metal element, and Pt, and a content of the group 14 metal element in terms of oxide in the dehydrogenation catalyst is 9% by mass or more and 50% by mass or less based on the total mass of the dehydrogenation catalyst.

5 Claims, No Drawings

METHOD FOR PRODUCING CONJUGATED DIENE

TECHNICAL FIELD

The present invention relates to a method for producing a conjugated diene.

BACKGROUND ART

An increase in the demand of a conjugated diene including butadiene as a raw material for synthetic rubbers, or the like has been anticipated because of motorization centering on Asia in recent years. For example, a method for subjecting n-butane to a direct dehydrogenation reaction using a dehydrogenation catalyst to produce a conjugated diene (Patent Literature 1) and a method for subjecting n-butene to an oxidative dehydrogenation reaction to produce a conjugated diene (Patent Literatures 2 to 4) have been known as a method for producing a conjugated diene.

CITATION LIST

Patent Literature

Patent Literature 1: Japanese Unexamined Patent Publication No. 2014-205135
Patent Literature 2: Japanese Unexamined Patent Publication No. S57-140730
Patent Literature 3: Japanese Unexamined Patent Publication No. S60-1139
Patent Literature 4: Japanese Unexamined Patent Publication No. 2003-220335

SUMMARY OF INVENTION

Technical Problem

Along with the increase in the demand of conjugated dienes, the development of various methods for producing conjugated dienes is required, the method having different features such as demand characteristics, operating cost, and reaction efficiency of a producing device.

An object of the present invention is to provide a method for producing a conjugated diene which provides less catalyst deterioration and can efficiently produce a conjugated diene from an olefin as a novel production method of a conjugated diene.

Solution to Problem

The present inventors have found that a specific dehydrogenation catalyst exhibits excellent dehydrogenation activity in the dehydrogenation reaction of an olefin and can maintain high dehydrogenation activity for a long period of time, and the present invention has thus been completed.

That is, a method for producing a conjugated diene according to one aspect of the present invention comprises a step of contacting a raw material gas containing an olefin with a dehydrogenation catalyst to obtain a product gas containing a conjugated diene. In the production method, the dehydrogenation catalyst contains Al, a group 14 metal element, and Pt, and a content of the group 14 metal element in terms of oxide in the dehydrogenation catalyst is 9% by mass or more and 50% by mass or less based on the total mass of the dehydrogenation catalyst.

According to the production method, catalyst deterioration is sufficiently suppressed, and the conjugated diene can be efficiently produced from the olefin.

In one aspect, the content of the group 14 metal element in terms of oxide in the dehydrogenation catalyst may be 11% by mass or more, or 15% by mass or more based on the total mass of the dehydrogenation catalyst. In this case, catalyst deterioration is more remarkably suppressed.

In one aspect, the group 14 metal element may be Sn. In this case, the above-mentioned effect is much more remarkably exhibited.

In one aspect, the dehydrogenation catalyst may be a catalyst having the group 14 metal element and Pt which are supported on a support containing Al. By using such a catalyst, the conjugated diene can be more efficiently obtained.

In one aspect, the olefin may be an olefin having 4 to 10 carbon atoms.

In one aspect, the olefin and the conjugated diene may be butene and butadiene, respectively. The production method can be particularly suitably employed as a method for producing butadiene.

Advantageous Effects of Invention

The present invention can provide a method for producing a conjugated diene which provides less catalyst deterioration and can efficiently produce a conjugated diene from an olefin as a novel producing route of a conjugated diene.

DESCRIPTION OF EMBODIMENTS

Hereinafter, one suitable embodiment of the present invention will be described. However, the present invention is not limited to the following embodiment at all.

A production method according to the present embodiment comprises a step of contacting a raw material gas containing an olefin with a dehydrogenation catalyst to obtain a product gas containing a conjugated diene. In the production method, the dehydrogenation catalyst contains aluminum (Al), a group 14 metal element, and platinum (Pt), and a content of the group 14 metal element in terms of oxide in the dehydrogenation catalyst is 9% by mass or more and 50% by mass or less based on the total mass of the dehydrogenation catalyst.

According to the production method according to the present embodiment, catalyst deterioration is sufficiently suppressed, and the conjugated diene can be efficiently produced from the olefin. That is, in the production method according to the present embodiment, catalyst deterioration is sufficiently suppressed, so that the replacement or reproduction frequency of the catalyst can be reduced. In the production method according to the present embodiment, the conversion rate of the olefin in a dehydrogenation reaction is high, and the selection rate of the conjugated diene is high, so that the conjugated diene can be obtained with a favorable yield.

Herein, the conversion rate of the olefin, the selection rate of the conjugated diene, and the yield of the conjugated diene are defined by the following formulae (1), (2), and (3).

$$R_C = \{1-(m_1/m_0)\} \times 100 \tag{1}$$

$$r_S = \{m_2/(m_0-m_1)\} \times 100 \tag{2}$$

$$r_Y = (m_2/m_0) \times 100 \tag{3}$$

$r_C$ in the formula (1) is the conversion rate of the olefin. $m_0$ is the number of moles of the olefin contained in the raw material gas. $m_1$ is the number of moles of the olefin remaining in the product gas.

$r_S$ in the formula (2) is the selection rate (%) of the conjugated diene. $m_2$ is the number of moles of the conjugated diene contained in a product material (product gas).

$r_Y$ in the formula (3) is the yield (%) of the conjugated diene.

In the production method according to the present embodiment, a cause for suppressing deterioration in the dehydrogenation catalyst and a cause for the dehydrogenation catalyst exhibiting excellent dehydrogenation activity are not necessarily clear, but the present inventors speculate as follows. That is, it is considered that an acid point derived from Al is covered with an oxide of the group 14 metal element, which causes reduction in acid property, thereby suppressing side reactions such as the cracking reaction and polymerization reaction of the olefin. It is considered that the group 14 metal element and Pt form bimetallic particles to dilute Pt atoms in the particles, so that the cleavage reaction of a C—C bond caused by the Pt atoms acting on one molecule of the olefin at multiple points is suppressed.

In the production method according to the present embodiment, the raw material gas contains the olefin. The number of carbon atoms of the olefin may be the same as that of the intended conjugated diene. That is, the olefin may be a hydrocarbon compound obtained when one of double bonds which are present in the conjugated diene assumed as a product material is hydrogenated. The number of carbon atoms of the olefin may be, for example, 4 to 10, or 4 to 6.

The olefin may be, for example, chain-like or cyclic. The chain-like olefin may be at least one selected from the group consisting of butene, pentene, hexene, heptene, octene, nonene, and decene, for example. The chain-like olefin may be linear or branched. The linear olefin may be at least one selected from the group consisting of n-butene, n-pentene, n-hexene, n-heptene, n-octene, n-nonene, and n-decene, for example. The branched olefin may be at least one selected from the group consisting of isopentene, 2-methylpentene, 3-methylpentene, 2,3-dimethylpentene, isoheptene, isooctene, isononene, and isodecene, for example. The raw material gas may contain the olefins singly or in combinations of two or more.

In the raw material gas, the partial pressure of the olefin may be 1.0 MPa or less, 0.1 MPa or less, or 0.01 MPa or less. By decreasing the partial pressure of the olefin of the raw material gas, the conversion rate of the olefin is likely to be further improved.

The partial pressure of the olefin in the raw material gas is preferably 0.001 MPa or more, and more preferably 0.005 MPa or more from the viewpoint of reducing the size of a reactor with respect to a raw material flow rate.

The raw material gas may further contain an inactive gas such as nitrogen or argon, and may further contain steam.

When the raw material gas contains the steam, the content of the steam is preferably 1.0 times moles or more, and more preferably 1.5 times moles or more with respect to the olefin. By incorporating the steam in the raw material gas, deterioration in the activity of the catalyst may be more remarkably suppressed. The content of the steam may be, for example, 50 times moles or less, and is preferably 10 times moles or less with respect to the olefin.

The raw material gas may further contain other ingredients such as hydrogen, oxygen, carbon monoxide, carbon dioxide, alkanes, and dienes in addition to the above.

In the production method according to the present embodiment, the product gas contains the conjugated diene. Examples of the conjugated diene obtained by the production method according to the present embodiment include 1,3-butadiene, 1,3-pentadiene, isoprene, 1,3-hexadiene, 1,3-heptadene, 1,3-octadiene, 1,3-nonadiene, and 1,3-decadiene.

The production method according to the present embodiment can be particularly suitably used for a method using a raw material gas containing butene as an olefin among the above, that is, a method for producing 1,3-butadiene. The butene used for producing 1,3-butadiene may be 1-butene or 2-butene. The butene may be a mixture of 1-butene and 2-butene. 2-butene may be one of, or both cis-2-butene and trans-2-butene.

In the production method according to the present embodiment, the product gas containing a conjugated diene is obtained by contacting the raw material gas with the dehydrogenation catalyst to generate the dehydrogenation reaction of the olefin.

In the present embodiment, the dehydrogenation catalyst contains Al, the group 14 metal element, and Pt. Herein, the group 14 metal element means a metal element belonging to the group 14 in a long-form element periodic table defined by the International Union of Pure and Applied Chemistry (IUPAC). The group 14 metal element may be at least one selected from the group consisting of tin (Sn) and lead (Pb), for example.

In the dehydrogenation catalyst, Al, the group 14 metal element, and Pt may be present as a single oxide, may be present as a composite oxide with other metal, or may be present as a metal salt or a metal simple substance.

In the dehydrogenation catalyst, the content $C_1$ of Al in terms of oxide may be 30% by mass or more, or 50% by mass or more based on the total mass of the dehydrogenation catalyst. The content $C_1$ may be 90% by mass or less.

In the dehydrogenation catalyst, the content $C_2$ of the group 14 metal element in terms of oxide is 9% by mass or more and 50% by mass or less based on the total mass of the dehydrogenation catalyst. When the content $C_2$ is less than 9% by mass, an effect of suppressing catalyst deterioration tends to be less likely to be obtained. When the content $C_2$ is more than 50% by mass, the exposure of a Pt active point is relatively decreased, so that sufficient dehydrogenation activity tends to be less likely to be obtained.

The content $C_2$ in the dehydrogenation catalyst is preferably 11% by mass or more, and more preferably 13% by mass or more, or may be 15% by mass or more, or 18% by mass or less, based on the total mass of the dehydrogenation catalyst. By using the dehydrogenation catalyst of the content $C_2$, catalyst deterioration tends to be more remarkably suppressed.

The content $C_2$ in the dehydrogenation catalyst is preferably 40% by mass or less, and more preferably 30% by mass or less, based on the total mass of the dehydrogenation catalyst. In the dehydrogenation catalyst of the content $C_2$, the exposure of the active point of Pt is moderately increased, so that higher dehydrogenation activity tends to be obtained.

In the dehydrogenation catalyst, the content $C_3$ of Pt (content in terms of Pt atoms) is preferably 0.05% by mass or more, and more preferably 0.2% by mass or more, based on the total mass of the dehydrogenation catalyst In the dehydrogenation catalyst, the amount of platinum per catalyst amount is increased, so that the size of a reactor can be reduced.

The content $C_3$ in the dehydrogenation catalyst is preferably 5.0% by mass or less, and more preferably 3.0% by mass or less, based on the total mass of the dehydrogenation catalyst. In such a dehydrogenation catalyst, Pt particles formed on the catalyst have a size suitable for the dehydrogenation reaction, to increase the surface area of platinum per unit platinum weight, so that a more efficient reaction system can be achieved.

In the dehydrogenation catalyst, the ratio ($C_2/C_1$) of the content $C_2$ to the content $C_1$ is preferably 0.05 or more, and more preferably 0.1 or more. The ratio ($C_2/C_1$) may be 0.6 or less, or 0.4 or less. When the ratio ($C_2/C_1$) is within this range, catalyst deterioration is further suppressed, so that the producing efficiency of the conjugated diene tends to be further improved.

In the dehydrogenation catalyst, the ratio ($C_3/C_1$) of the content $C_3$ to the content $C_1$ is preferably 0.003 or more, and more preferably 0.005 or more. The ratio ($C_3/C_1$) may be 0.05 or less, or 0.03 or less. When the ratio ($C_3/C_1$) is within this range, a side reaction is further suppressed, so that the producing efficiency of the conjugated diene tends to be further improved.

In the dehydrogenation catalyst, the ratio ($C_3/C_2$) of the content $C_3$ to the content $C_2$ is preferably 0.005 or more, and more preferably 0.01 or more. The ratio ($C_3/C_2$) may be 0.3 or less, or 0.1 or less. When the ratio ($C_3/C_2$) is within this range, a side reaction is further suppressed, so that the producing efficiency of the conjugated diene tends to be further improved.

The contents of Al, group 14 metal element, and Pt in the dehydrogenation catalyst can be analyzed and confirmed by a method shown in the following Examples.

The dehydrogenation catalyst may contain other metal elements in addition to Al, the group 14 metal element, and Pt. Examples of the other metal elements include Li, Na, K, Mg, Ca, Zn, Fe, In, Se, Sb, Ni, and Ga.

The dehydrogenation catalyst may have a metal oxide support and an active metal supported on the metal oxide support, for example.

In one aspect, the dehydrogenation catalyst may be a catalyst in which active metals containing a group 14 metal element and Pt are supported on a metal oxide support containing Al.

In another aspect, the dehydrogenation catalyst may be a catalyst in which an active metal containing Pt is supported on a metal oxide support containing Al and a group 14 metal element.

The metal oxide support may be a support containing alumina ($Al_2O_3$), or a support containing a composite oxide of Al and another metal, for example. More specifically, the metal oxide support may be a support containing a metal oxide such as alumina, a composite oxide of. Al and Mg, a composite oxide of Al and Sn, a composite oxide of Al and Pb, or a composite oxide of Al and Zn, Se, Fe or In or the like, for example. The metal oxide support may contain the metal oxides singly or in combinations of two or more.

Examples of a method for preparing the support include, but not particularly limited to, a sol gel method, a coprecipitation method, and a hydrothermal synthesis method.

One aspect of the method for preparing the support will be shown below. First, a solution in which a metal precursor of an intended metal element is dissolved in a solvent is prepared. Next, ion exchange water is dropped into the solution while the solution is stirred. Then, the solution is stirred while the solution is heated under reflux, to hydrolyze the metal precursor, and the solvent is then removed under reduced pressure to obtain a solid. By drying the obtained solid, and thereafter firing the dried solid, the support containing the intended metal element is obtained. When a support containing a plurality of metal elements is prepared, a mixed solution may be used, which is obtained by preparing a solution in which a metal precursor is dissolved in a solvent for each of the plurality of metal elements, and mixing the solutions. By dissolving metal precursors of a plurality of metal elements in the same solvent, a mixed solution may be prepared.

The precursor of the metal element may be a salt or complex containing the metal element, for example. The salt containing the metal element may be at least one selected from the group consisting of an inorganic salt, an organic acid salt, and hydrates thereof, for example. The inorganic salt may be at least one selected from the group consisting of a sulfate, a nitrate, a chloride, a phosphate, and a carbonate, for example. The organic salt may be at least one selected from the group consisting of an acetate and an oxalate, for example. The complex containing the metal element may be at least one selected from the group consisting of an alkoxide complex and an ammine complex, for example.

The solvent dissolving the metal precursor may be at least one selected from the group consisting of hydrochloric acid, nitric acid, ammonia water, and ethanol, for example.

Firing can be performed under air atmosphere or oxygen environment, for example. Firing may be performed at one stage, or multi stages of two stages or more. A firing temperature may be a temperature at which a metal precursor can be decomposed. The firing temperature may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

In one aspect, the metal oxide support may be a support containing alumina. In this aspect, the content of Al in terms of oxide in the metal oxide support may be 20% by mass or more, or 50% by mass or more, based on the total mass of the metal oxide support.

In another aspect, the metal oxide support may be a support containing a composite oxide of Al and Mg. In this aspect, the content of Al in terms of oxide in the metal oxide support may be 20% by mass or more, 50% by mass or more, 99% by mass or less, or 95% by mass or less, based on the total mass of the metal oxide support. In this aspect, the content of Mg in terms of oxide in the metal oxide support may be 1.0% by mass or more, 5.0% by mass or more, 80% by mass or less, or 50% by mass or less, based on the total mass of the metal oxide support.

In still another aspect, the metal oxide support may be a support containing a composite oxide of Al and Sn. In this aspect, the content of Al in terms of oxide in the metal oxide support may be 20% by mass or more, 50% by mass or more, 99% by mass or less, or 95% by mass or less, based on the total mass of the metal oxide support. In this aspect, the content of Sn in terms of oxide in the metal oxide support may be 5.0% by mass or more, 10% by mass or more, 50% by mass or less, or 30% by mass or less, based on the total mass of the metal oxide support.

The acidity of the metal oxide support is preferably near neutrality from the viewpoint of suppressing a side reaction. Herein, the standard over the acidity of the metal oxide support is generally distinguished by a pH in a state where the metal oxide support is dispersed in water. That is, herein, the acidity of the metal oxide support can be represented by the pH of a suspension in which 1% by mass of the metal oxide support is suspended. The acidity of the metal oxide support may preferably have a pH of 5.5 to 8.5, and more preferably a pH of 6.0 to 8.0.

The specific surface area of the metal oxide support is preferably 30 m$^2$/g or more, and more preferably 50 m$^2$/g or more. The metal oxide support can advantageously produce the conjugated diene at high efficiency. The specific surface area of the metal oxide support may be 1000 m$^2$/g or less, or 500 m$^2$/g or less. The metal oxide support having such a specific surface area tends to have sufficient strength which can be suitably used industrially, so that the conjugated diene tends to be produced at higher efficiency. The specific surface area of the metal oxide support is measured with a BET specific surface area meter using a nitrogen adsorption method.

The dehydrogenation catalyst may be a catalyst having one or two or more of metals supported on the metal oxide support. A metal supported on the metal oxide support (hereinafter, also referred to as a "supported metal") may be supported as an oxide or a simple substance metal.

Examples of the supported metal supported on the metal oxide support include Pt, a group 14 metal element, Li, Na, K, Mg, Ca, Zn, Fe, In, Se, Sb, Ni, and Ga. In the present embodiment, when the metal oxide support does not contain the group 14 metal element, Pt and the group 14 metal element are contained in the supported metal. When the metal oxide contains the group 14 metal element, the supported metal may contain Pt.

Examples of a method for supporting the metal on the metal oxide support include, but not particularly limited to, an impregnation method, a precipitation method, a coprecipitation method, a kneading method, an ionic exchange method, and a pore-filling method.

One aspect of the method for supporting the metal on the metal oxide support will be shown below. First, a metal oxide support is added into a solution in which a precursor of an intended supported metal is dissolved in a solvent (for example, alcohol), and the solution is then stirred. Then, the solvent is removed under reduced pressure to obtain a solid, and the solid is dried. By firing the dried solid, the intended metal can be supported on the support.

In the supporting method, the precursor of the supported metal may be a salt or complex containing the metal element, for example. The salt containing the metal element may be at least one selected from the group consisting of an inorganic salt, an organic acid salt, and hydrates thereof, for example. The inorganic salt may be at least one selected from the group consisting of a sulfate, a nitrate, a chloride, a phosphate, and a carbonate, for example. The organic salt may be at least one selected from the group consisting of an acetate and an oxalate, for example. The complex containing the metal element may be at least one selected from the group consisting of an alkoxide complex and an ammine complex, for example.

As conditions during stirring, for example, a stirring temperature can be set to 0 to 60° C., and a stirring time can be set to 10 minutes to 24 hours. As conditions during drying, for example, a drying temperature can be set to 100 to 250° C., and a drying time can be set to 3 hours to 24 hours.

Firing can be performed under air atmosphere or oxygen environment, for example. Firing may be performed at one stage, or multi stages of two stages or more. A firing temperature may be a temperature at which a precursor of a supported metal can be decomposed. The firing temperature may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

The amount of Pt supported on the support (content of Pt in the dehydrogenation catalyst) is preferably 0.01 parts by mass or more, and more preferably 0.1 parts by mass or more with respect to 100 parts by mass of the support. The amount of Pt supported on the support may be 5.0 parts by mass or less, or 3.0 parts by mass or less with respect to 100 parts by mass of the support. In such an amount of Pt, Pt particles formed on the catalyst have a size suitable for the dehydrogenation reaction, to increase the surface area of platinum per unit platinum weight, so that a more efficient reaction system can be achieved. In such an amount of Pt, high activity can be maintained over a longer period of time while catalyst cost is suppressed.

The degree of dispersion of Pt in the dehydrogenation catalyst may be 1.0% or more, and preferably 5.0% or more. By the dehydrogenation catalyst having such a degree of dispersion of Pt, a side reaction is further suppressed, so that high activity tends to be maintained over a longer period of time. The degree of dispersion of Pt represents a value measured by a measuring method described in the following Examples.

In one suitable aspect, the dehydrogenation catalyst may be a catalyst having a group 14 metal element and Pt supported on a metal oxide support containing Al (preferably, a metal oxide support containing alumina), or a catalyst having a group 14 metal element and Pt supported in this order.

In this aspect, the amount of the group 14 metal element supported on the support is preferably 5.0 parts by mass or more, and more preferably 10 parts by mass or more with respect to 100 parts by mass of the support. The amount of the group 14 metal element supported on the support may be 80 parts by mass or less, or 50 parts by mass or less with respect to 100 parts by mass of the support. When the amount of the group 14 metal element is within the range, catalyst deterioration is further suppressed, so that high activity tends to be maintained over a longer period of time.

The dehydrogenation catalyst may be molded by methods such as an extrusion molding method and a tablet compression method.

The dehydrogenation catalyst may contain a molding auxiliary agent in the range not to deteriorate the physical properties and catalytic performance of the catalyst from the viewpoint of improving moldability in a molding step. The molding auxiliary agent may be at least one selected from the group consisting of a thickener, a surfactant, a humectant, a plasticizer, and a binder raw material, for example. The molding step of molding the dehydrogenation catalyst may be performed at a suitable stage during the producing step of the dehydrogenation catalyst with consideration of the reactivity of the molding auxiliary agent.

The shape of the molded dehydrogenation catalyst is not particularly limited, and can be appropriately selected according to a form for using the catalyst. For example, the shape of the dehydrogenation catalyst may be a shape such as a pellet shape, a granular shape, a honeycomb shape, or a sponge shape.

The dehydrogenation catalyst to be used may be subjected to a reduction treatment as a pretreatment. The reduction treatment can be performed in a state where the dehydrogenation catalyst is held at 40 to 600° C. under reducing gas atmosphere, for example. A holding time may be 0.05 to 24 hours, for example. The reducing gas may be hydrogen and carbon monoxide or the like, for example.

By using the dehydrogenation catalyst subjected to the reduction treatment, the induction period at an initial stage of a dehydrogenation reaction can be shortened. The induction period at the initial stage of the reaction means a state where there are very few active metals that have been reduced and activated, among active metals contained in the catalyst, and the activity of the catalyst is low.

The production method according to the present embodiment includes a step of contacting a raw material gas with a dehydrogenation catalyst, and the step can be conducted using a reactor filled with the dehydrogenation catalyst, for example. In the step, a conjugated diene is produced according to the dehydrogenation reaction of an olefin contained in the raw material gas.

As the reactor, various reactors used for a gas phase reaction using a solid catalyst can be used. Examples of the reactor include a fixed-bed insulation type reactor, a radial flow type reactor, and a tube-type reactor.

The reaction form of the dehydrogenation reaction may be a fixed-bed type, a moving-bed type, or a fluidized-bed type, for example. Among these, a fixed-bed type is preferred from the viewpoint of equipment cost.

From the viewpoint of reaction efficiency, the reaction temperature of the dehydrogenation reaction, i.e., the temperature in the reactor may be 300 to 800° C., 400 to 700° C., or 500 to 650° C. When the reaction temperature is 300° C. or higher, the balanced conversion rate of the olefin is not excessively low, so that the yield of the conjugated diene tends to be further improved. When the reaction temperature is 800° C. or lower, a caulking speed is not excessively high, so that the high activity of the dehydrogenation catalyst tends to be maintained over a longer period of time.

The reaction pressure, i.e., the atmospheric pressure in the reactor may be 0.01 to 1 MPa, 0.05 to 0.8 MPa, or 0.1 to 0.5 MPa. When the reaction pressure is within the range, the dehydrogenation reaction is likely to proceed, so that more excellent reaction efficiency tends to be obtained.

When the above step is performed in a continuous reaction form for continuously supplying a raw material gas, the ratio (hereinafter, referred to as "W/F") of the mass W of the dehydrogenation catalyst to the supply rate (supply amount/time) F of the raw material gas may be, for example, 0.001 g·min·ml$^{-1}$ or more, or 0.01 g·min·ml$^{-1}$ or more. The ratio W/F of the range can further increase the conversion rate of the olefin. The ratio W/F may be 20 g·min·ml$^{-1}$ or less, or 2.0 g·min·ml$^{-1}$ or less. The ratio W/F of the range can further decrease the size of the reactor. The amounts of the raw material gas and catalyst to be used may be appropriately selected in a more preferable range according to reaction conditions and the activity of the catalyst, or the like, and the ratio W/F is not limited to the range.

As described above, the production method according to the present embodiment provides less catalyst deterioration, and can efficiently produce the conjugated diene from the olefin. Therefore, the production method according to the present embodiment can reduce the frequency of catalyst reproduction. Because of this, the production method according to the present embodiment is very useful when the conjugated diene is industrially produced.

While the suitable embodiment of the present invention has been described above, the present invention is not limited to the embodiment.

EXAMPLES

Hereinafter, the present invention will be more specifically described with reference to Examples, but the present invention is not limited to Examples.

Catalyst Synthesis Example 1

<Preparation of Catalyst Precursor A-1>

A solution in which 0.90 g SnCl$_2$.2H$_2$O was dissolved in 50 mL of EtOH was added into 2.0 g of an alumina support classified to 20 to 60 meshes (NEOBEADS GB-13, manufactured by Mizusawa Industrial Chemicals, Ltd., pH of a suspension having a concentration of 1% by mass in water: 7.9). The obtained mixed solution was stirred at room temperature for 30 minutes using a rotary evaporator, and EtOH was then removed under reduced pressure. The obtained solid was dried at 130° C. in an oven overnight. Next, the dried solid was fired at three stages (at 130° C. for 30 minutes, at 550° C. for 3 hours, and at 800° C. for 3 hours) under an air flow to obtain a catalyst precursor A-1 in which Sn was supported on an alumina support.

<Preparation of Catalyst A-1>

2.0 g of a catalyst precursor A-1, and an aqueous solution in which 53.6 mg of H$_2$PtCl$_6$.2H$_2$O was dissolved in 11 mL of water were mixed. The obtained mixed solution was stirred at 40° C. for 30 minutes using a rotary evaporator, and water was then removed under reduced pressure while the mixed solution was stirred. The obtained solid was dried at 130° C. in an oven overnight. Next, the dried solid was fired at two stages (at 130° C. for 30 minutes, and at 550° C. for 3 hours) under an air flow, and then subjected to hydrogen reduction at 550° C. for 3 hours, to obtain a catalyst A-1.

In the obtained catalyst A-1, the content $C_2$ of Sn in terms of oxide was 23.0% by mass based on the total mass of the catalyst; the content $C_3$ of Pt was 1.0% by mass based on the total mass of the catalyst; and the content $C_1$ of Al in terms of oxide was 76.0% by mass based on the total mass of the catalyst. In the catalyst A-1, the degree of dispersion of Pt was 9.1%.

[Analysis Method of Catalyst]

In the present Examples, the content of Sn in terms of oxide in the catalyst, the content of Pt, and the content of Al in terms of oxide were measured with an X-ray fluorescence analysis method (XRF). The X-ray fluorescence analysis was performed using a measuring device PW2400 (manufactured by PANalytical), and the content was quantified using standardless quantitative calculation program Uni-Quant4. A measurement sample for XRF was prepared as follows. 125 mg of a sample (for example, catalyst A-1), and 125 mg of cellulose (binder) were measured in an agate mortar, and mixed for 15 minutes to obtain a mixture, and the mixture was then put into a tablet molding machine having a diameter of 20 mm, to subject the mixture to pressure molding on conditions of 300 kgf·cm$^{-2}$ for 10 minutes.

The degree of dispersion of Pt was measured by a method for measuring the degree of dispersion of metal using CO as adsorption species. A device and measurement conditions or the like will be shown below.

Device: device for measuring degree of dispersion of metal R-6011 manufactured by Ohkura Riken Co., LTD.

Gas flow rate: 30 mL/min (helium, hydrogen)

Amount of sample: about 0.1 g (precisely measured to four decimal places)

Pretreatment: A temperature was risen to 400° C. over 1 hour under a hydrogen stream, to perform a reduction treatment at 400° C. for 60 minutes. The gas was then changed from hydrogen to helium, to purge the hydrogen at 400° C. for 30 minutes, and the temperature was then decreased to room temperature under a helium stream. After a detector was stabilized at room temperature, CO pulsing was performed.

Measurement conditions: Carbon monoxide was pulse-injected by 0.0929 cm$^3$ at room temperature (27° C.) under a stream of normal pressure helium gas to measure the amount of adsorption thereof. The adsorption was performed a number of times until the adsorption was saturated (at least 3 times, at most 15 times).

Catalyst Synthesis Example 2

In preparing a catalyst precursor, a catalyst was prepared in the same manner as in Catalyst Synthesis Example 1 except that the blending amount of $SnCl_2 \cdot 2H_2O$ was set to 0.62 g to afford a catalyst A-2.

In the obtained catalyst A-2, the content $C_2$ of Sn in terms of oxide was 17.0% by mass based on the total mass of the catalyst; the content $C_3$ of Pt was 1.0% by mass based on the total mass of the catalyst; and the content $C_1$ of Al in terms of oxide was 82.0% by mass based on the total mass of the catalyst. In the catalyst A-2, the degree of dispersion of Pt was 15.3%.

Catalyst Synthesis Example 3

In preparing a catalyst precursor, a catalyst was prepared in the same manner as in Catalyst Synthesis Example 1 except that the blending amount of $SnCl_2 \cdot 2H_2O$ was set to 0.45 g to afford a catalyst A-3.

In the obtained catalyst A-3, the content $C_2$ of Sn in terms of oxide was 13.0% by mass based on the total mass of the catalyst; the content $C_3$ of Pt was 1.0% by mass based on the total mass of the catalyst; and the content $C_1$ of Al in terms of oxide was 86.0% by mass based on the total mass of the catalyst. In the catalyst A-3, the degree of dispersion of Pt was 26.2%.

Catalyst Synthesis Example 4

In preparing a catalyst precursor, a catalyst was prepared in the same manner as in Catalyst Synthesis Example 1 except that the blending amount of $SnCl_2 \cdot 2H_2O$ was set to 0.37 g to afford a catalyst A-4.

In the obtained catalyst A-4, the content $C_2$ of Sn in terms of oxide was 11.0% by mass based on the total mass of the catalyst; the content $C_3$ of Pt was 1.0% by mass based on the total mass of the catalyst; and the content $C_1$ of Al in terms of oxide was 88.0% by mass based on the total mass of the catalyst. In the catalyst A-4, the degree of dispersion of Pt was 34.1%.

Catalyst Synthesis Example 5

In preparing a catalyst precursor, a catalyst was prepared in the same manner as in Catalyst Synthesis Example 1 except that the blending amount of $SnCl_2 \cdot 2H_2O$ was set to 0.24 g to afford a catalyst A-5.

In the obtained catalyst A-5, the content $C_2$ of Sn in terms of oxide was 7.4% by mass based on the total mass of the catalyst; the content $C_3$ of Pt was 1.0% by mass based on the total mass of the catalyst; and the content $C_1$ of Al in terms of oxide was 91.6% by mass based on the total mass of the catalyst. In the catalyst A-4, the degree of dispersion of Pt was 32.9%.

Catalyst Synthesis Example 6

A catalyst B-1 was obtained in the same manner as in Catalyst Synthesis Example 1 except that 2.0 g of an alumina support classified to 20 to 60 meshes (NEOBEADS GB-13, manufactured by Mizusawa Industrial Chemicals, Ltd.) was used in place of the catalyst precursor A-1 (that is, a Sn-supporting step was omitted).

In the obtained catalyst B-1, the content $C_3$ of Pt was 1.0% by mass based on the total mass of the catalyst; and the content $C_1$ of Al in terms of oxide was 99.0% by mass based on the total mass of the catalyst. In the catalyst B-1, the degree of dispersion of Pt was 3.8%.

Example 1

A tube-type reactor was filled with 0.5 g of a catalyst A-1, and the reactor was connected to a fixed-bed circulation type reaction device. Next, while a mixed gas of hydrogen and He (hydrogen:He=4:6 (mole ratio)) was circulated at a rate of 50 mL/min, the temperature of the reactor was raised to 550° C., and the reactor was held at the temperature for 1 hour. Then, a mixed gas (raw material gas) of 1-butene, He, and water was supplied to the reactor, to subject 1-butene in the raw material gas to a dehydrogenation reaction. Herein, the mole ratio of 1-butene, He, and water in the raw material gas was adjusted to 1:4:3. The supply rate of the raw material gas to the reactor was adjusted to 99 mL/min. A contact time W/F was adjusted to 0.04 g-cat·min·mL$^{-1}$. The pressure of the raw material gas of the reactor was adjusted to atmospheric pressure.

At a point of time when 20 minutes elapsed from the start of the reaction, a product material (product gas) of the dehydrogenation reaction was extracted from the tube-type reactor. At a point of time when 360 minutes elapsed from the start of the reaction, a product material (product gas) of the dehydrogenation reaction was extracted from the tube-type reactor. At the start of the reaction, the supply of the raw material gas was started. The product gas extracted at each time was analyzed using a gas chromatograph (TCD-GC) provided with a thermal conductivity detector. As a result of analysis, the product gas was confirmed to contain 1,3-butadiene. The concentration (unit: % by mass) of butene and the concentration (unit: % by mass) of 1,3-butadiene in the product gas extracted at each time were quantified based on the gas chromatograph.

From the concentration of butene and the concentration of 1,3-butadiene in the product gas, the conversion rate of the raw material (conversion rate of butene), the selection rate of 1,3-butadiene (butadiene selection rate), and the yield of 1,3-butadiene (butadiene yield) at each time were calculated. The conversion rate of butene is defined by the following formula (4); the selection rate of 1,3-butadiene is defined by the following formula (5); and the yield of 1,3-butadiene is defined by the following formula (6).

$$R_c = (1 - M_P/M_0) \times 100 \quad (4)$$

$$R_S = M_b/(M_0 - M_P) \times 100 \quad (5)$$

$$R_Y = M_b/M_0 \times 100 \quad (6)$$

$R_c$ in the formula (4) is the butene conversion rate. $R_S$ in the formula (5) is the butadiene selection rate. $R_Y$ in the formula (6) is the butadiene yield. $M_0$ in the formulae (4) to (6) is the number of moles of 1-butene in the raw material gas. $M_P$ in the formulae (4) and (5) is the number of moles of 1-butene, t-2-butene, and c-2-butene in the product gas. $M_b$ in the formulae (5) and (6) is the number of moles of 1,3-butadiene in the product gas.

As a result of calculation, at a point of time when 20 minutes elapsed, the butene conversion rate was 19.2%; the butadiene selection rate was 95.7%; and the butadiene yield was 18.4%. At a point of time when 360 minutes elapsed, the butene conversion rate was 19.0%; the butadiene selection rate was 96.0%; and the butadiene yield was 18.2%.

Example 2

The dehydrogenation reaction of 1-butene and the analysis of a product gas were performed by the same operation as that of Example 1 except that a catalyst A-2 was used in place of the catalyst A-1. At a point of time when 20 minutes elapsed from the start of the reaction, a butene conversion rate was 27.7%; a butadiene selection rate was 77.5%; and a butadiene yield was 21.5%. At a point of time when 360 minutes elapsed, a butene conversion rate was 27.3%; a butadiene selection rate was 87.7%; and a butadiene yield was 23.9%.

Example 3

The dehydrogenation reaction of 1-butene and the analysis of a product gas were performed by the same operation as that of Example 1 except that a catalyst A-3 was used in place of the catalyst A-1. At a point of time when 20 minutes elapsed from the start of the reaction, a butene conversion rate was 28.1%; a butadiene selection rate was 76.0%; and a butadiene yield was 21.4%. At a point of time when 360 minutes elapsed, a butene conversion rate was 19.3%; a butadiene selection rate was 93.0%; and a butadiene yield was 17.9%.

Example 4

The dehydrogenation reaction of 1-butene and the analysis of a product gas were performed by the same operation as that of Example 1 except that a catalyst A-4 was used in place of the catalyst A-1. At a point of time when 20 minutes elapsed from the start of the reaction, a butene conversion rate was 26.9%; a butadiene selection rate was 79.1%; and a butadiene yield was 21.3%. At a point of time when 360 minutes elapsed, a butene conversion rate was 15.7%; a butadiene selection rate was 93.0%; and a butadiene yield was 14.6%.

Comparative Example 1

The dehydrogenation reaction of 1-butene and the analysis of a product gas were performed by the same operation as that of Example 1 except that a catalyst A-5 was used in place of the catalyst A-1. At a point of time when 20 minutes elapsed from the start of the reaction, a butene conversion rate was 24.8%; a butadiene selection rate was 82.6%; and a butadiene yield was 20.5%. At a point of time when 360 minutes elapsed, a butene conversion rate was 8.8%; a butadiene selection rate was 89.5%; and a butadiene yield was 7.9%.

Comparative Example 2

The dehydrogenation reaction of 1-butene and the analysis of a product gas were performed by the same operation as that of Example 1 except that a catalyst B-1 was used in place of the catalyst A-1. At a point of time when 20 minutes elapsed from the start of the reaction, a butene conversion rate was 17.9%; a butadiene selection rate was 7.9%; and a butadiene yield was 1.4%. At a point of time when 360 minutes elapsed, a butene conversion rate was 10.6%; a butadiene selection rate was 11.9%; and a butadiene yield was 1.3%.

The results of Examples 1 to 4 and Comparative Examples 1 and 2 are shown in Table 1.

TABLE 1

| | | Example 1 | Example 2 | Example 3 | Example 4 | Comparative Example 1 | Comparative Example 2 |
|---|---|---|---|---|---|---|---|
| Catalyst compositions | Dehydrogenation catalyst | Catalyst A-1 | Catalyst A-2 | Catalyst A-3 | Catalyst A-4 | Catalyst A-5 | Catalyst B-1 |
| | Amount of Pt (% by mass) | 1.0 | 1.0 | 1.0 | 1.0 | 1.0 | 1.0 |
| | Amount of $SnO_2$ (% by mass) | 23.0 | 17.0 | 13.0 | 11.0 | 7.4 | 0.0 |
| | Amount $Al_2O_3$ (% by mass) | 76.0 | 82.0 | 86.0 | 88.0 | 91.6 | 99.0 |
| | Degree of dispersion of Pt (%) | 9.1 | 15.3 | 26.2 | 34.1 | 32.9 | 3.8 |
| Reaction conditions | Temperature (° C.) | | | | 550 | | |
| | Pressure (MPaG) | | | | 0 | | |
| | W/F (g-cat · min · $ml^{-1}$) | | | | 0.04 | | |
| | Raw material mixing ratio (mole ratio) $C_4$/He/$H_2O$ | | | | 1:4:3 | | |
| Evaluation results | Butene conversion rate (%) After 20 minutes | 19.2 | 27.7 | 28.1 | 26.9 | 24.8 | 17.9 |
| | After 360 minutes | 19.0 | 27.3 | 19.3 | 15.7 | 8.8 | 10.6 |
| | Butadiene selection rate (%) After 20 minutes | 95.7 | 77.5 | 76.0 | 79.1 | 82.6 | 7.9 |
| | After 360 minutes | 96.0 | 87.7 | 93.0 | 93.0 | 89.5 | 11.9 |
| | Butadiene yield (%) After 20 minutes | 18.4 | 21.5 | 21.4 | 21.3 | 20.5 | 1.4 |
| | After 360 minutes | 18.2 | 23.9 | 17.9 | 14.6 | 7.9 | 1.3 |
| | (Yield after 360 minutes)/(Yield after 20 minutes) | 0.99 | 1.12 | 0.84 | 0.69 | 0.38 | 0.89 |

Reference Example 1

The dehydrogenation reaction of n-butane was performed by the same operation as that of Example 1 except that a mixed gas of n-butane, He, and water was used as a raw material gas.

At a point of time when 20 minutes elapsed from the start of the reaction, a product material (product gas) of a dehydrogenation reaction was extracted from a tube-type reactor. At a point of time when 360 minutes elapsed from the start of the reaction, a product material (product gas) of the dehydrogenation reaction was extracted from the tube-type reactor. The product gas extracted at each time was analyzed using a gas chromatograph (TCD-GC) provided with a thermal conductivity detector. As a result of analysis, the product gas was confirmed to contain 1,3-butadiene. The concentration (unit: % by mass) of n-butane and the concentration (unit: % by mass) of 1,3-butadiene in the product gas extracted at each time were quantified based on the gas chromatograph.

From the concentrations of n-butane and 1,3-butadiene in the product gas, the conversion rate of the raw material (conversion rate of n-butane), the selection rate of 1,3-butadiene, and the yield of 1,3-butadiene at each time were calculated. The conversion rate of n-butane is defined by the following formula (7); the selection rate of 1,3-butadiene is defined by the following formula (8); and the yield of 1,3-butadiene is defined by the following formula (9).

$$R'_c = (1 - M'_P/M'_0) \times 100 \quad (7)$$

$$R'_S = M_b/(M'_0 - M'_P) \times 100 \quad (8)$$

$$R'_Y = M_b/M'_0 \times 100 \quad (9)$$

$R'_c$ in the formula (7) is the conversion rate of n-butane. $R'_S$ in the formula (8) is the selection rate of 1,3-butadiene. $R'_Y$ in the formula (9) is the yield of 1,3-butadiene. $M'_0$ in the formulae (7) to (9) is the number of moles of n-butane in the raw material gas. $M'_P$ in the formulae (7) and (8) is the number of moles of n-butane in the product gas. $M_b$ in the formulae (8) and (9) is the number of moles of 1,3-butadiene in the product gas.

As a result of calculation, at a point of time when 20 minutes elapsed, the conversion rate of n-butane was 2.1%; the selection rate of 1,3-butadiene was 25.2%; and the yield of 1,3-butadiene was 0.5%. At a point of time when 360 minutes elapsed, the conversion of n-butane was hardly observed.

Reference Example 2

The dehydrogenation reaction of n-butane and the analysis of a product gas were performed by the same operation as that of Reference Example 1 except that a catalyst A-5 was used in place of the catalyst A-1. At a point of time when 20 minutes elapsed from the start of the reaction, the conversion rate of n-butane was 50.7%; the selection rate of 1,3-butadiene was 13.2%; and the yield of 1,3-butadiene was 6.7%. At a point of time when 360 minutes elapsed, the conversion rate of n-butane was 27.3%; the selection rate of 1,3-butadiene was 20.4%; and the yield of 1,3-butadiene was 5.6%.

As shown in Reference Examples 1 and 2, in the dehydrogenation reaction using the alkane as the raw material, the catalyst A-1 was even poorer in reaction efficiency than the catalyst A-5. On the other hand, as shown in Examples and Comparative Examples, in the dehydrogenation reaction using the olefin as the raw material, the catalyst A-1 had less catalyst deterioration than that of the catalyst A-5, and could more efficiently produce the conjugated diene.

The invention claimed is:

1. A method for producing a conjugated diene, comprising contacting a raw material gas containing an olefin with a dehydrogenation catalyst to obtain a product gas containing a conjugated diene, wherein
    the dehydrogenation catalyst is a catalyst having a group 14 metal element and Pt supported on a support containing Al, and
    a content of the group 14 metal element in terms of oxide in the dehydrogenation catalyst is 13% by mass or more and 50% by mass or less based on the total mass of the dehydrogenation catalyst.

2. The production method according to claim 1, wherein the group 14 metal element is Sn.

3. The production method according to claim 1, wherein the content of the group 14 metal element in terms of oxide in the dehydrogenation catalyst is 15% by mass or more and 50% by mass or less based on the total mass of the dehydrogenation catalyst.

4. The method according to claim 1, wherein the olefin is an olefin having 4 to 10 carbon atoms.

5. The production method according to claim 1, wherein the olefin is butene, and the conjugated diene is butadiene.

* * * * *